(12) United States Patent
Haupt et al.

(10) Patent No.: US 11,970,696 B1
(45) Date of Patent: Apr. 30, 2024

(54) OPTICAL METHODS AND SYSTEMS FOR DNA ASSEMBLY FOR COMPUTER DATA STORAGE

(71) Applicant: Leidos, Inc., Reston, VA (US)

(72) Inventors: Steven Gerald Haupt, San Diego, CA (US); Stephen Alan Chappell, San Diego, CA (US)

(73) Assignee: Leidos, Inc., Reston, VA (US)

( * ) Notice: Subject to any disclaimer, the term of this patent is extended or adjusted under 35 U.S.C. 154(b) by 533 days.

(21) Appl. No.: 17/004,675

(22) Filed: Aug. 27, 2020

Related U.S. Application Data

(60) Provisional application No. 62/892,385, filed on Aug. 27, 2019.

(51) Int. Cl.
*C12N 15/10* (2006.01)
*G16B 50/00* (2019.01)

(52) U.S. Cl.
CPC ......... *C12N 15/1068* (2013.01); *G16B 50/00* (2019.02)

(58) Field of Classification Search
CPC .................................................. G16B 50/00
See application file for complete search history.

(56) References Cited

U.S. PATENT DOCUMENTS

| | | | |
|---|---|---|---|
| 8,808,986 | B2 | 8/2014 | Jacobson et al. |
| 11,550,939 | B2 * | 1/2023 | Peck ........................ G16B 50/00 |
| 2005/0170281 | A1 * | 5/2005 | Stengele et al. ......... C27H 21/00 |
| 2005/0249396 | A1 * | 11/2005 | Cerrina et al. ...... G02B 19/0023 |
| 2015/0361422 | A1 * | 12/2015 | Sampson et al. ........ C12N 15/10 |
| 2018/0137418 | A1 | 5/2018 | Roquet et al. |

FOREIGN PATENT DOCUMENTS

| | | |
|---|---|---|
| WO | WO 2018/118998 A1 * | 6/2018 |
| WO | WO 2019/145713 | 8/2019 |

OTHER PUBLICATIONS

Carlson "Maintenance Tips: UV Scanners", posted Aug. 11, 2017; 7 sheets downloaded from https://www.cpilink.com/blog/maintenance-tips-uv_scanners on Sep. 10, 2022 (Year: 2017).*
Hirao et al. Most compact hairpin-turn structure exerted by a short DNA fragment, d(GCGAAGC) in solution: an extraordinarily stable structure resistant to nucleases and heat. Nucleic Acids Res. Feb. 25, 1994;22(4):576-82. doi: 10.1093/nar/22.4.576 (Year: 1994).*
Dong, et al., "DNA Storage: Research Landscape and Future Prospects," National Science Review, vol. 7, Issue 6, pp. 1092-1107, Jun. 2020.
Kosuri, et al., "Large-Scale de novo DNA Synthesis: Technologies and Applications," Nat. Methods 11, pp. 499-507, 2014.
Bryan Bishop, et al., "Summary Report, Technology Working Group Meeting on Future DNA Synthesis Technologies," held in Arlington, VA on Sep. 14, 2017, (prepared) Oct. 22, 2017, 39 pages (annotated by LAC).
Organick L., et al., "Random access in large-scale DNA data storage," Nat. Biotechnol., vol. 36, No. 3, pp. 242-248, Mar. 2018.

* cited by examiner

*Primary Examiner* — Lori A. Clow
(74) *Attorney, Agent, or Firm* — Dawn-Marie Bey; Bey & Cotropia PLLC

(57) ABSTRACT

An array-based system of assembled DNA for computer data storage is described. An array surface contains immobilized seed DNA initially having with blunt (or blocked) ends with a photocleavable optical linker at a forward end thereof holding the last few base pairs. A light source is light is applied to break the linker, generating a sticky end which allows for hybridization. Data-bearing DNA cassettes are introduced to the array and attach via their sticky ends to the unblock sites on the array surface. The attachment is made permanent via ligase.

7 Claims, 12 Drawing Sheets
Specification includes a Sequence Listing.

| binary values | Oligomer Cassette Set A DNA sequence used to represent binary data with attachment sequences | Oligomer Cassette Set B DNA sequence used to represent binary data with attachment sequences | Oligomer Cassette Set C DNA sequence used to represent binary data with attachment sequences |
|---|---|---|---|
| 000 | 3'AAGG CAC ATTG5'<br>5'GTG TAAC3'<br>(SEQ ID NO: 2) | 3'ATTG CAC GCAT5'<br>5'GTG CGTA3'<br>(SEQ ID NO: 10) | 3'GCAT CAC AAGG 5'<br>5'GTG TTCC3'<br>(SEQ ID NO: 18) |
| 001 | 3'AAGG CAT ATTG5'<br>5' GTA TAAC3'<br>(SEQ ID NO: 3) | 3'ATTG CAT GCAT5'<br>5' GTA CGTA 3'<br>(SEQ ID NO: 11) | 3'GCAT CAT AAGG 5'<br>5'GTA TTCC3'<br>(SEQ ID NO: 19) |
| 010 | 3'AAGG CTA ATTG5'<br>5'GAT TAAC3'<br>(SEQ ID NO: 4) | 3'ATTG CTA GCAT5'<br>5'GAT CGTA 3'<br>(SEQ ID NO: 12) | 3'GCAT CTA AAGG 5'<br>5'GAT TTCC 3'<br>(SEQ ID NO: 20) |
| 011 | 3'AAGG CTG ATTG5'<br>5'GAC TAAC3'<br>(SEQ ID NO: 5) | 3'ATTG CTG GCAT5'<br>5'GAC CGTA 3'<br>(SEQ ID NO: 13) | 3'GCAT CTG AAGG 5'<br>5'GAC TTCC 3'<br>(SEQ ID NO: 21) |
| 100 | 3'AAGGTCG ATTG5'<br>5'GTG TAAC3'<br>(SEQ ID NO: 6) | 3'ATTG TCG GCAT5'<br>5'GTG CGTA 3'<br>(SEQ ID NO: 14) | 3'GCAT TCG AAGG 5'<br>5'GTG TTCC 3'<br>(SEQ ID NO: 22) |
| 101 | 3'AAGG TCA ATTG5'<br>5'GTG TAAC3'<br>(SEQ ID NO: 7) | 3'ATTG TCA GCAT5'<br>5'GTG CGTA 3'<br>(SEQ ID NO: 15) | 3'GCAT TCA AAGG 5'<br>5'GTG TTCC 3'<br>(SEQ ID NO: 23) |
| 110 | 3'AAGG TGC ATTG5'<br>5'GTG TAAC3'<br>(SEQ ID NO: 8) | 3'ATTGTGC GCAT5'<br>5'GTG CGTA 3'<br>(SEQ ID NO: 16) | 3'GCAT TGC AAGG 5'<br>5'GTG TTCC 3'<br>(SEQ ID NO: 24) |
| 111 | 3'AAGG TGT ATTG5'<br>5'GTG TAAC3'<br>(SEQ ID NO: 9) | 3'ATTG TGT GCAT5'<br>5'GTG CGTA 3'<br>(SEQ ID NO: 17) | 3'GCAT TGT AAGG 5'<br>5'GTG TTCC 3'<br>(SEQ ID NO: 25) |

Figure 1b

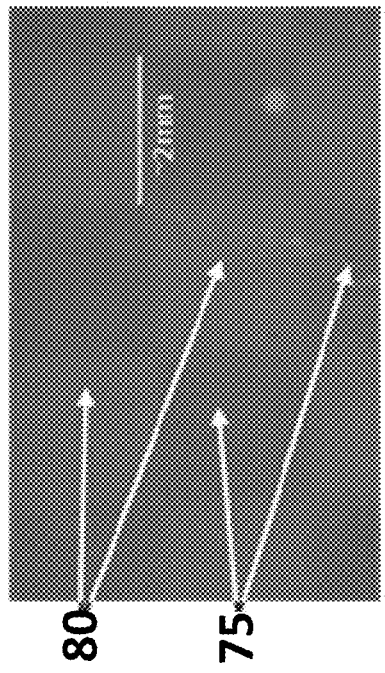
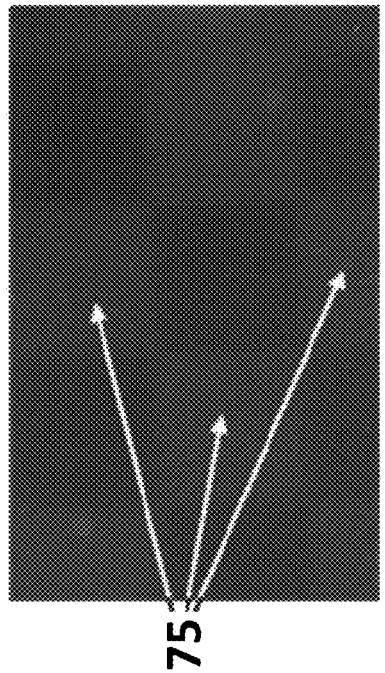

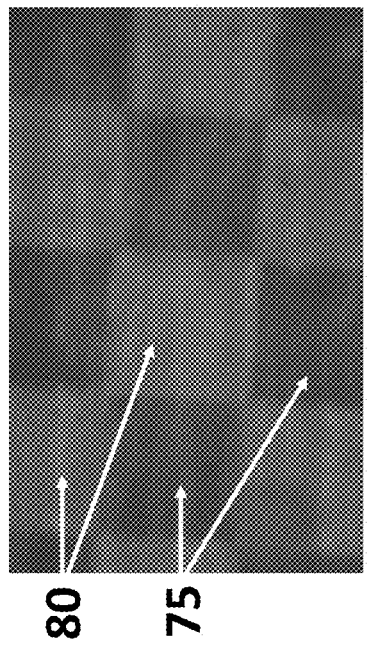
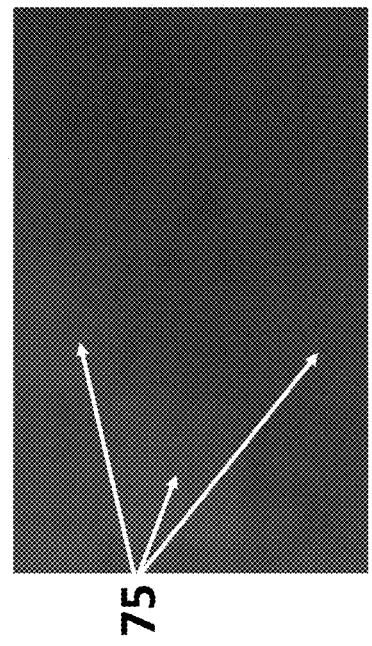

OPTICAL METHODS AND SYSTEMS FOR DNA ASSEMBLY FOR COMPUTER DATA STORAGE

CROSS-REFERENCE TO RELATED APPLICATIONS

This application claims benefit of priority to U.S. Provisional Application No. 62/892,385 entitled "Optical Methods For DNA Assembly For Computer Data Storage" filed Aug. 27, 2019 which is incorporated herein by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,916 Byte ASCII (Text) file named "2020-11-03_38898-202_SQL_ST25.txt," created on Nov. 3, 2020.

BACKGROUND OF THE EMBODIMENTS

Field of the Embodiments

The present embodiments relate generally to improved techniques for DNA assembly synthesis and storage of data thereon.

Description of Related Art

By all accounts, the world is generating more digital computer data than the present storage capacity can handle. An emerging and evolving solution may be use of DNA as storage mechanism. While we know we can store data this way, issues of costs, efficiency and scalability remain. The following article provides a detailed summary of past and current efforts to make DNA storage a viable option and its contents are incorporated herein by reference: DNA storage: research landscape and future prospects by Dong et al., National Science Review 7: 1092-1107, 2020 (advance access publication 21 Jan. 2020). The motivation for using DNA for data storage includes size and stability. The high level process for end-to-end storage and retrieval of digital information in DNA includes primary steps of: converting digital files in any format to binary code, encoding binary data in digital DNA sequence bases, synthesizing (writing) physical DNA molecule from digital DNA sequence, reading (sequencing) physical DNA molecule and generate digital DNA sequence bases, decoding digital DNA sequence bases to binary data and converting binary data into readable digital files. Of these primary steps, synthesis remains a bottle neck in the overall process.

A common method for DNA synthesis is the amidite process on a column. This process is unsuitable for the DNA data storage application for a number of reasons. This is essentially a serial process that is limited to generating hundreds to thousands of strands of DNA when millions are required. The reagents used in this method limit potential for oligomer synthesis beyond 200 nts (nucleotides). The reagents are toxic and limit syntheses to laboratory conditions. The amidite oligo synthesis process is referenced in the article entitled Large-scale de novo DNA synthesis: technologies and applications. Nat Methods 2014; 11: 499-507 by Kosuri et al. the contents of which is incorporated herein by reference in its entirety.

New enzymatic methods are being developed that have their own limitations. A ligation process is reported where small pieces of DNA and ligase are dispensed using a piezo system. The disadvantage with this process is that the reactions need to be confined to individual sites and this requires dispensing reagent into wells across kilometers of disposable tape and is not scalable. U.S. Pat. No. 8,808,986 entitled Methods and devices for high fidelity polynucleotide synthesis which is incorporated herein by reference in its entirety describes such an exemplary method and system.

Another emerging technique developed by Evonetix, is to use a heater chip to control amidite growth as described in, for example, International Application No. WO2019145713A1 which is incorporated herein by references. However, the heater chip currently available is limited to 10,000 oligomers and falls short of required throughput by orders of magnitude.

Exemplary background literature includes patent documents for Nucleic acid-based data storage found at US Patent Application Publication No. US20180137418A1 and Oligonucleotide and nucleic acid synthesis found at UK Patent Application Publication No. GB201801182D0, the substance of which are incorporated herein by reference in their entireties. Additionally, the Summary Report from Technology Working Group Meeting on future DNA synthesis technologies (Sep. 14, 2017, Arlington, VA) highlights previous, current and possible future avenues for improving DNA synthesis technologies.

SUMMARY OF EMBODIMENTS

In a first exemplary embodiment, a data storage system includes: a surface array including thereon multiple strands of immobilized DNA sequences, wherein a first end of each of the multiple strands is attached to the surface array and a second end of each of the multiple strands is blunt, further wherein each of the second ends of each of the multiple strands includes a photocleavable optical linker approximate thereto; an optical source for directing light to the surface array in a predetermined pattern, wherein when the light interacts with a photocleavable optical linker near a second end of a strand, a sticky end of the second end is exposed; and means for introducing data-encoded DNA cassettes to the surface array, wherein each of the data-encoded DNA cassettes attaches to an exposed sticky end.

In a second exemplary embodiment, a process for DNA-based data storage includes: immobilizing multiple seed DNA strands in on a surface of a chip, each strand of seed DNA including a first attached end and a second exposed end, wherein the second exposed end is blunt and contains a photocleavable optical linker; directing light a first time to the array to break multiple of the photocleavable optical linkers at the second ends of multiple seed DNA strands in a first predetermined pattern thereby exposing a sticky end of each of the multiple seed DNA strands exposed to the light; and introducing first data-encoded DNA cassettes to the surface of the chip, wherein each of the first data-encoded DNA cassette includes a photocleavable optical linker at an end thereof, and further wherein each of at least a portion of the first data-encoded DNA cassettes attach to an exposed sticky end of a seed DNA strand.

In a third exemplary embodiment, a printer for printing data-encoded DNA for data storage, includes: at least one cartridge holder for holding a removable cartridge, the removable cartridge containing: a first outward facing surface containing an array of immobilized seed DNA strands thereon, each strand of seed DNA including a first attached end and a second exposed end, wherein the second exposed end is blunt and contains a photocleavable optical linker; a series of wells, each of the series of wells having an opening facing a back of the first outward facing surface containing the array, wherein each of the wells contains data-encoded DNA cassettes; at least one optical scanner source for scanning a light signal directed at the first outward facing surface containing the array in a first predetermined pattern to break multiple of the photocleavable optical linkers at the second ends of multiple seed DNA strands thereby exposing a sticky end of each of the multiple seed DNA strands exposed to the light; and a liquid pumping system for introducing first data-encoded DNA cassettes from at least a first well in the series of wells to the array, wherein each of the first data-encoded DNA cassette includes a photocleavable optical linker at an end thereof, and further wherein each of at least a portion of the first data-encoded DNA cassettes attach to an exposed sticky end of a seed DNA strand.

BRIEF DESCRIPTION OF FIGURES

The patent or application file contains at least one figure executed in color and/or a photograph. Copies of this patent or patent application publication with color drawing(s) and/or photographs will be provided by the Office upon request and payment of the necessary fee.

FIGS. 1a and 1b show Set DNA sequences used to represent binary data with attachment sequences in accordance with an exemplary embodiment herein;

FIGS. 6a and 6b show actual results from carrying out certain steps of the process of FIGS. 2a and 2b;

FIGS. 7a and 7b show actual results from carrying out certain steps of the process of FIGS. 2a and 2b.

DETAILED DESCRIPTION

Figure 1A:
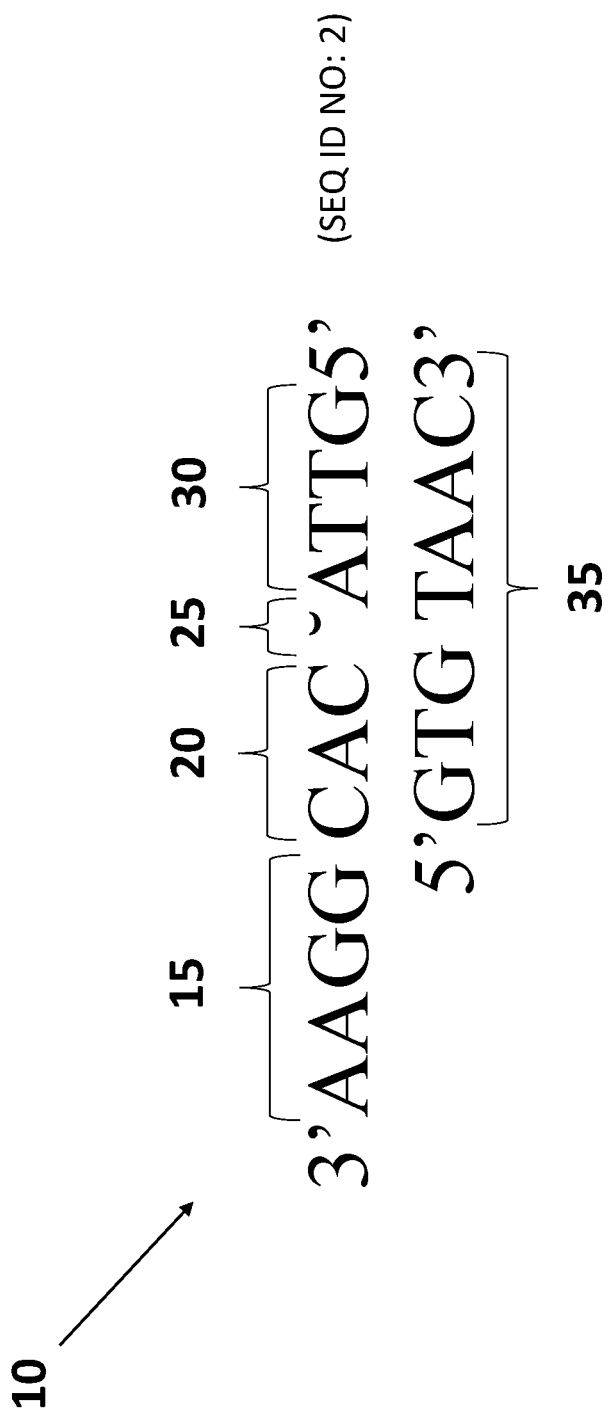

The purpose of the embodiments described herein is production and use of an array based system of DNA assembly for the purpose of computer data storage. In this application assembled DNA sequences are used to represent computer binary data. The motivation for this approach is multifold. DNA has the capacity to store huge amounts of information in a small physical footprint; over 200 Petabytes of data could be stored in a gram of DNA, which occupies a volume of less than a teaspoon. This is approximately 10 times all the data, both digital and printed, currently held by the library of congress. Additionally, DNA has long term stability with half-life over 500 years, also making it attractive for use as a long-term data storage medium. The current challenge in using DNA for data storage is that a very large variety of DNA oligomers must be made in a highly parallel-process to be practical. The current methods of DNA synthesis are not suitable for this application.

Accordingly, in the present embodiments, we use a method of light based chemistry that allows for the controlled addition of DNA cassettes across an array of base DNA oligomers. This method has the advantage of simplicity of the fluidics and controlled growth over millions of reaction sites.

In this process DNA is synthesized to represent digital data. The first steps are to take the digital data consisting as zeros and ones, and convert it into DNA sequence data. For the present embodiments, a predetermined set of DNA oligomers represent the binary data (see Table 1), not individual base pairs. For an example of known methods for storing data in synthesized DNA, see Storing data in oligonucleotides is described in Organick L, Ang S D, Chen Y et al. Random access in large-scale DNA data storage. Nat Biotechnol 2018; 36: 242-8 which is incorporated herein by reference in its entirety. Next, the DNA is assembled on an array of reaction sites with each DNA addition representing a set of digital data. Short sequences of several base pairs are used to represent bit values. In the specific embodiment discussed herein, we used 2 sets of 4 oligomers, to allow 2 bits per addition cycle. But this process could be used to add more bits per addition cycle. A pool consisting of three sets of 8 oligomers in each set can be used to encode 3 bits per addition, and a larger reagent pool consisting of 3 sets of 16 oligomers in each set allows each addition to add 4 bits.

An example of how binary values of 3 bits in length can be represented as a DNA sequence is shown in Table 1. This is just an example; other DNA sequences can be used in practice.

TABLE 1

| binary values | DNA sequence used to represent binary data forward strand |
|---|---|
| 000 | CAC |
| 001 | CAT |
| 010 | CTA |
| 011 | CTG |
| 100 | TCG |
| 101 | TCA |
| 110 | TGC |
| 111 | TGT |

For example, a binary stream of 24 bits is first broken into 8 sets of 3 bits. Then using a lookup table, e.g., Table 1, it is converted to DNA sequence as shown in the example in Table 2.

TABLE 2

| | 24 bit data: | | | | | | | |
|---|---|---|---|---|---|---|---|---|
| | 011 | 110 | 111 | 100 | 111 | 101 | 101 | 111 |
| DNA equivalent: | CTG | TGC | TGT | TCG | TGT | TCA | TCA | TGT |

To allow attachment to the immobilized DNA array, the oligomer also has a binding sequence at the front and back end to allow for hybridization. For example, the front binding sequence for one set could be AAGG, the back ATTG. The complete 3' to 5' sequence would consist of the leading DNA for attachment to the immobilized DNA on the array, the data DNA, followed by a second set of attachment DNA for adding a subsequent round. Between the data sequence and the second set of binding sequence is an optical linker that is designated as: "⌢" as shown in FIG. 1a. The purpose of the optical linker is described further herein. In addition, the cassettes consist of double strand DNA and have the reverse complement. Accordingly, as shown in FIG. 1a, in the example herein, each oligomer cassette 10 includes the following combination of components: leading DNA 15, the data DNA 20, optical linker 25, attachment or trailing DNA 30 and the reverse complement DNA 35.

For the present example, the full reagent pool shown in FIG. 1b consists of three sets of oligomer cassettes referred as sets A, B, and C. Set A has a leading binding site that hybridizes to set C trailing DNA. The trailing DNA of set A binds to the leading sequence on set B. Set B has a trailing sequence that binds to the leading set of C. With these three sets of binding sequences, DNA can be assembled in an ABCABC . . . Pattern. The full set reagent pool of 24 DNA cassettes has the sequence diversity needed to convey any arbitrary binary data.

The DNA is synthesized as large pools of oligomers, with each oligomer type representing a small portion of the binary data. This requires synthesizing millions of specific DNA oligomers and requires a parallel process to be practical. A critical feature of the present process is the use of light based chemistry and equipment that allows the DNA synthesis process to be performed quickly and in parallel over millions of reaction sites with no segregation of reaction sites required. These attributes make this an ideal method for applying DNA for the computer data storage application.

A primary step in the embodied process is controlling growth on an array in a manner that facilitates parallel processing. Initially, the process starts with an array of immobilized DNA with blunt ends. DNA is considered to have a blunt end when both the forward and reverse strands are equal length. It is very difficult to ligate a second dsDNA oligomer to a blunt end. To address this difficulty, the present embodiments hold the last few base pairs using an optical linker. If a reaction is desired, the optical linker is broken with light, the last few base pairs are removed, leaving an open stretch or "sticky end" that allows for hybridization. The dsDNA representing digital data is then free to add where the array is treated with light, i.e., the sticky end, and is prevented from addition at the location with blunt ends. The addition is then made permanent with ligase that repairs the two nicks.

Figure 2A:
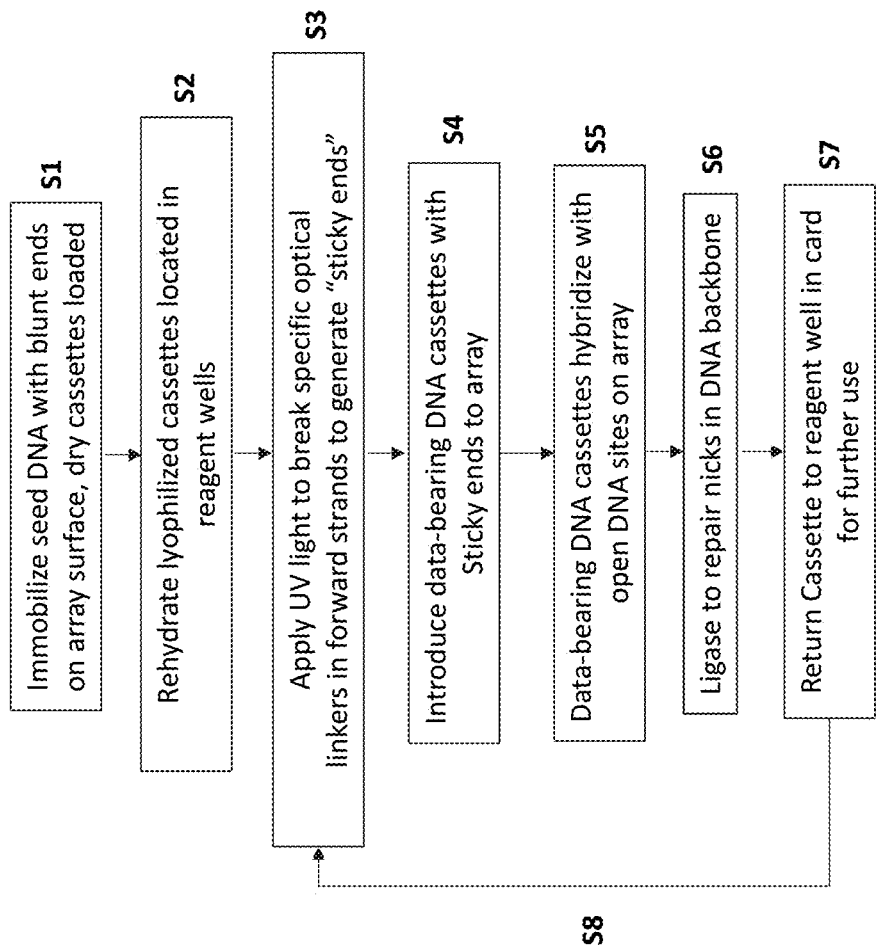
FIGS. 2a and 2b show a summary of the process whereby DNA is synthesized to represent digital data in accordance with an exemplary embodiments herein.
Figure 2B:
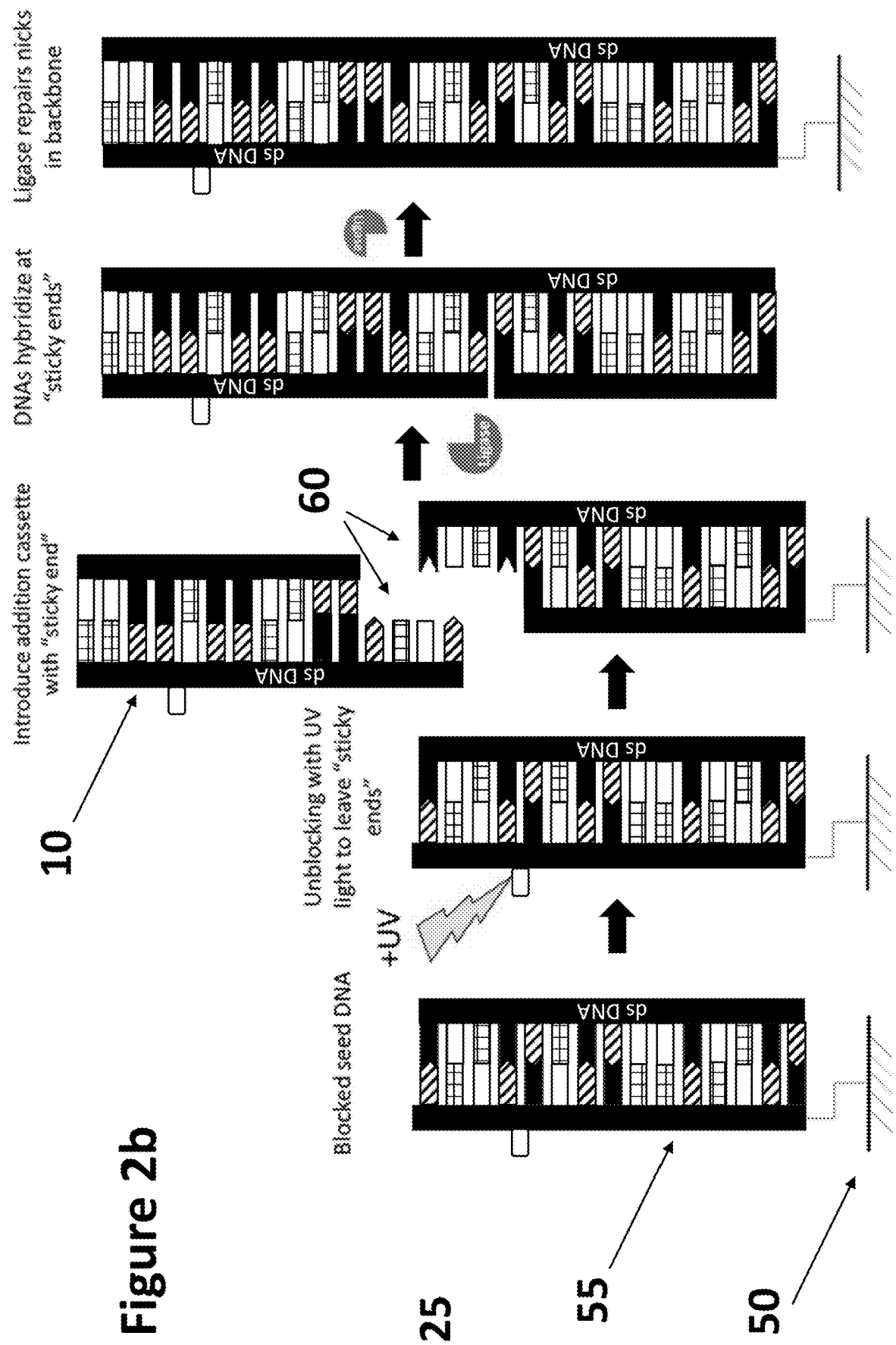

A summary of this process is shown and illustrated in FIGS. 2a and 2b. The array surface, i.e., chip, 50 is covered with immobilized seed DNA 55 with blunt, i.e., blocked, ends S1 prior to cartridge (or card) assembly. The card is then assembled to include lyophilized data-bearing DNA cassettes, enzyme and the array containing immobilized seed DNA. The data storage dsDNA oligomers are generated by the system as follows. The first step is the dry reagents from individual reagent wells are reconstituted by pumping water to the reagent wells S2 (see FIG. 4d) by activating valves on the cartridge. The forward strand of each piece of immobilized DNA on the array has a photocleavable optical linker 25 holding the last few base pairs. UV light is applied to break the linker, generating a "sticky end" 60 that allows for hybridization S3. Data-bearing DNA cassettes in the reconstituted reagent solution are introduced to the array S4 and the DNA cassettes conveying binary data are free to add to the exposed sites at their respective sticky ends 60, S5. The attachment is made permanent via ligase S6. Each added cassette has its own optical linker and is ready for a subsequent addition when desired. After the addition process, the unused (unattached) cassettes are returned to the reagent well they came from S7. The entire process is repeated using the next cassette pool (from next reagent well) until the full set of DNA is assembled S8.

Figure 3:
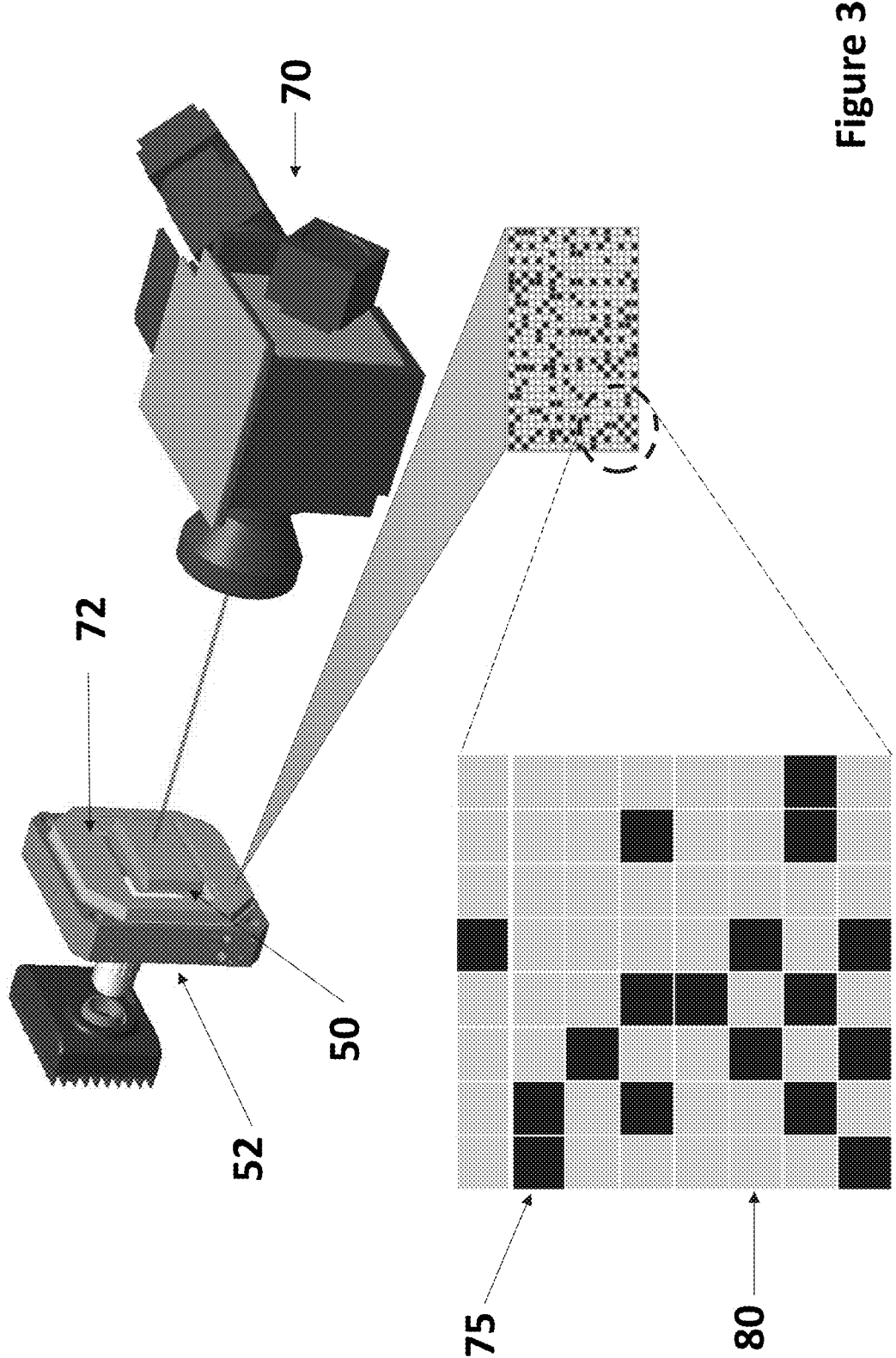
FIG. 3 shows a schematic of a first exemplary system for implementing the process of FIGS. 2a and 2b.

To make this chemistry practical, a light source that can direct light to millions of pixels is necessary. As shown in FIG. 3, in the exemplary embodiments discussed herein, a Digital Light Processor (DLP), or other appropriate programmable light source 70 is used to direct light to an array 50 which starts with seed DNA 55 (FIG. 2b) immobilized on glass or silicon. As shown and as discussed further with respect to FIGS. 4a to 4d, the array 50 may be inserted in an array holder 52 and may be removed once data storage is complete and replaced with a new array. One skilled in the art will appreciate that other types of Spatial Light Modulator (SLM) could also be used to direct light to the array surface. These devices are capable of directing millions of pixels of light instantly and over very small feature sizes. In the present embodiments, each pixel of dark 75 corresponds to a reaction site, i.e., the light impinges on the optical linker located at the pixel and, if not previously broken, the light breaks the link. Accordingly, data-bearing DNA cassettes which are flowing over the array 50 can selectively bind to the sticky ends of the immobilized DNA resulting from the break in the optical linker at the reaction site. Whereas array pixels which are not illuminated, i.e., light pixels 80, which include immobilized DNA with an intact optical linker are inert and will not bind to any data-bearing DNA cassettes as there is no exposed sticky end. Accordingly, the programmable light source 70, such as a DLP or SLM, capable of controlling light at the pixel level, is used to control data-bearing DNA additions at each reaction site in an array 50. At the time of filing of the present application, the state-of-the-art DLP is capable of generating approximately 4 million reaction sites on the order of 30 to 100 m in size.

Additionally, each incoming data-bearing DNA cassette also has an optical linker and the process can be repeated in cycles until a long dsDNA oligomer is formed. These series of data-bearing DNA additions are used to encode digital data to each oligomer strand. At the end of the process millions of unique DNA strands are generated across the array that represent the digital data.

Figure 4A:
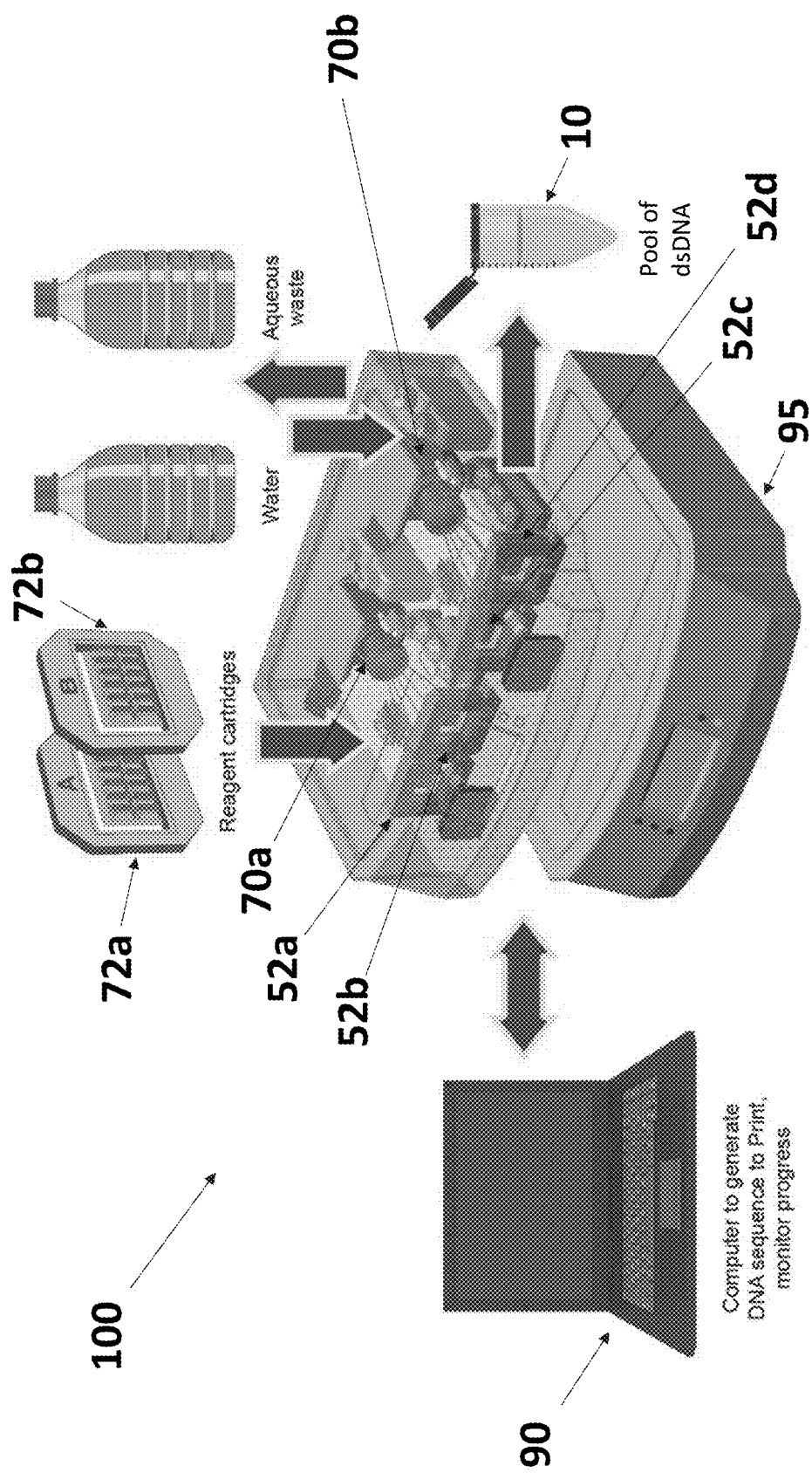
FIGS. 4a, 4b, 4c and 4d show schematic views of a second exemplary system for implementing the process of FIGS. 2a and 2b which includes the first exemplary system of FIG. 3.
Figure 4B:
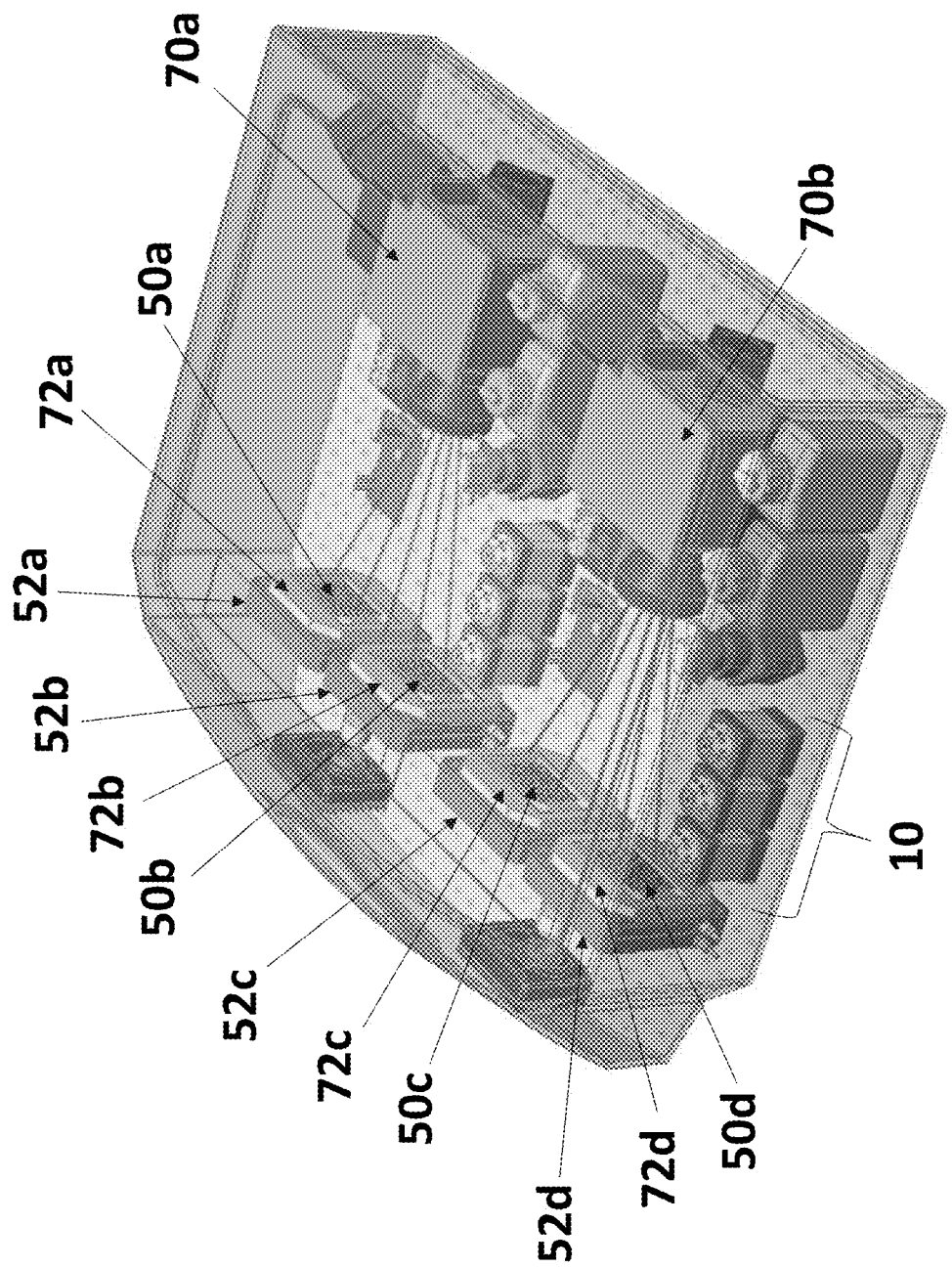

Referring to FIGS. 4a, 4b, 4c and 4d, an exemplary system for DNA printed data storage 100 is shown. In this exemplary system, a processor 90 generates the DNA sequence to print on a DNA storage printer 95. Within DNA storage printer 95, this exemplary system includes two DLPs 70a and 70b which are programmed to create reaction sites sequentially or simultaneously on dual arrays 50a, 50b and 50c, 50d, respectively (shown in FIG. 4b). As discussed above, reagent cartridges 72a, 72b, include the arrays 50a, 50b which are pre-seeded with inert, blunt ended DNAs containing photocleavable optical linkers 25. The reagent cartridges 72a, 72b are inserted within array holders 52a and 52b to be illuminated by DLP 70a as shown in FIG. 4b. The DLPs illuminate specific features in these arrays to break the photocleavable linkers to generate "sticky ends" that permit specific hybridization of incoming data-bearing DNA cassettes. The data-bearing DNA cassettes are introduced to the array from the reagent pools at the back of the cartridges 72a, 72b after rehydration using water and a valve/pumping system (not shown) as described in FIG. 2a. Hybridized DNAs are then permanently linked via DNA ligase. The inclusion of a photocleavable optical linker in each added data-bearing DNA cassette permits subsequent addition of additional data bearing DNA cassettes. Similarly, array holders 52c, 52d would each receive a reagent cartridge 72c, 72d to be illuminated by DLPs 70b.

Figure 4D:
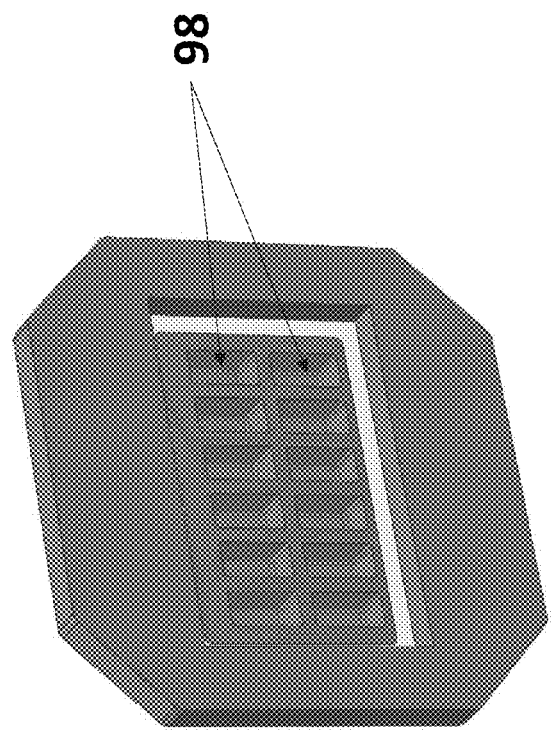
Figure 4C:
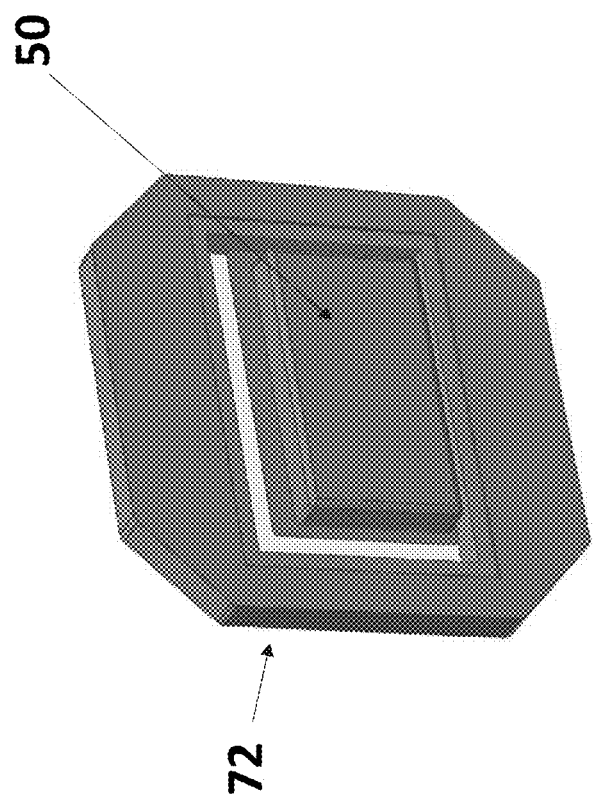

FIGS. 4c and 4d show front (4c) and back (4d) views of an exemplary reagent cartridge 72. The front side of the cartridge shown in FIG. 4c contains the array that faces the DLP (as shown in FIG. 3). In the back of the cartridge are reagent wells 98 where the cassettes are stored. The reagent wells 98 are of sufficient volume to allow reagent stored therein to flood the entire surface of the array 50. A pump (not shown) is first used to transfer water to reconstitute the dry cassettes located in the wells 98. The reagents are then transferred from the reagent wells 98 to the array 50 as needed by the pump.

Figures 5A, 5B:
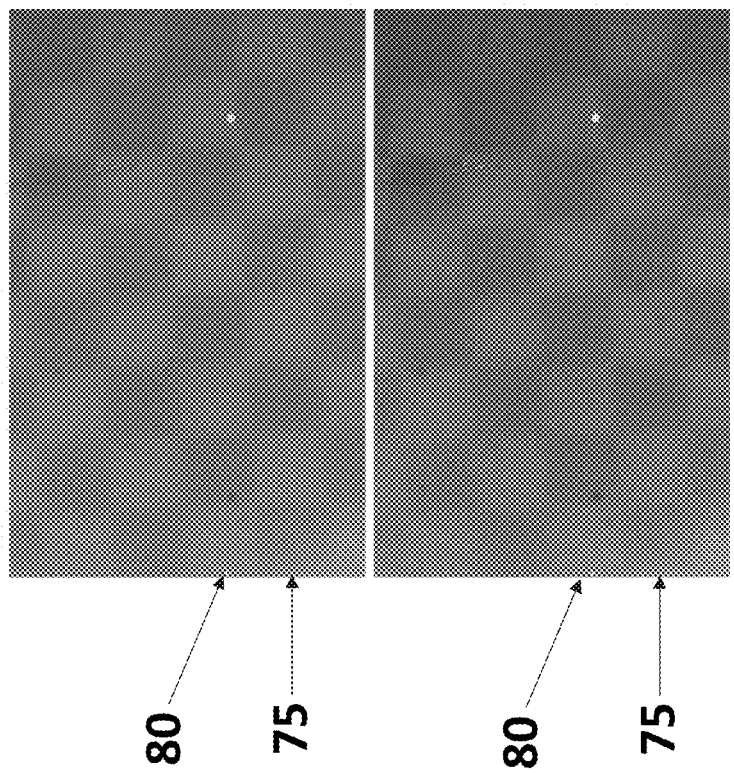
FIGS. 5a and 5b show actual results from carrying out certain steps of the process of FIGS. 2a and 2b.

The method described herein for the controlled addition of DNA cassettes across an array of base DNA oligomers has been proven out in experimental settings. In FIGS. 5a and 5b, the base concepts described herein of establishing an array of photo-cleavable base DNA having optical linkers and breaking the links in a predetermined pattern using a DLP are shown. In the proof of concept experiment, 25 uM of fresh biotinylated ss Cy3 photocleavable linker was hybridized to a glass streptavidin slide for 20 min. The base DNA having the sequence (SEQ ID NO: 1):

/iCy3/CTCACAACCCCAGAAA/iSpPC/CAGA-CATGCTTCCTGACATACGATATCTGTGA GCT-TAATGTCCTTATGT/3Bio/

Next, the slide containing the hybridized base DNA is exposed to UV light (250-310 nm) using a DLP in 5 by 5 pixel (5×5 pixel is equivalent to 1334×1334 μm) pattern for 15 minutes. FIGS. 5a and 5b show actual images of the resulting pattern imaged with a fluorescent microscope at 4× magnification. The pattern results from every other pixel (75 and 80) having an exposed sticky end responsive to breaking the optical linker.

In FIGS. 6a and 6b, a continuation of the example above with respect to FIGS. 5a and 5b, show actual images of the same slide portions before (FIG. 6a) and after (FIG. 6b) DNA reagent is introduced to an array of base DNA, wherein alternating pixels have exposed sticky ends from exposure to UV light (250-310 nm) from the DLP. Specifically, FIG. 6a shows a pattern of alternating pixels wherein for pixels 75 the Cy3 label is removed from seed DNA by the DLP light and thus exposed (deprotected) for ligation with DNA reagent and for pixels 80, the Cy3 remains immobilized. And FIG. 6b shows that at the same pixels, 75, the Cy5 labeled cassette is ligated to the deprotected base DNA. Similar to the ss Cy3 hybridization showing proof of concept in FIG. 5a, the array of FIGS. 6a and 6b includes base DNA formed using 25 uM of fresh biotinylated dsDNA Cy3 photocleavable linker hybridized to a glass streptavidin slide for 20 min, followed by introduction of dsCy5 reagent set (cassette) which ligates to the unprotected sites at the illuminated pixels.

The outcomes illustrated in FIGS. 6a and 6b were reproduced in accordance with the following specific experimental set up with results shown in FIGS. 7a and 7b.

1. 20 uM of biotinylated ds Cy3 photocleavable linker hybridized to a glass streptavidin slide for 30 min.
   a. The ds DNA used for this hybridization was annealed in a separate 200 uL single tube reaction with a 1:3 ratio of ssCy3:ssComp in an ABI 9600 thermocycler as follows:
      95 C 2 min→55 C 5 min→37 C 5 Min→22 C 5 min→4 C 5 min
2. Imaged the array under Cy3 and Cy5 wavelengths using Olympus IX51 Fluorescent Microscope (blank slide)
3. The array was exposed to 10 min of UV light (250-310 nm) in a 10×10 mm checkerboard pattern using a DLP.
4. 100 uM of ds Cy5 photocleavable linker cassette was added to the array.
5. The Cy5 ds cassette was hybridized as follows:
   a. Array (whole glass slide) was placed in 52 C hyb oven for 5 min
   b. Moved to 37 C Hyb oven 5 min
   c. RT 5 min on bench
   d. Placed in 4 C for 5 min
6. Array was rinsed 3× with 1× binding buffer
7. Imaged using Olympus IX51 Fluorescent Microscope at 4× magnification under Cy3 (FIG. 7a) and Cy5 (FIG. 7b) filters.

Figure 8:
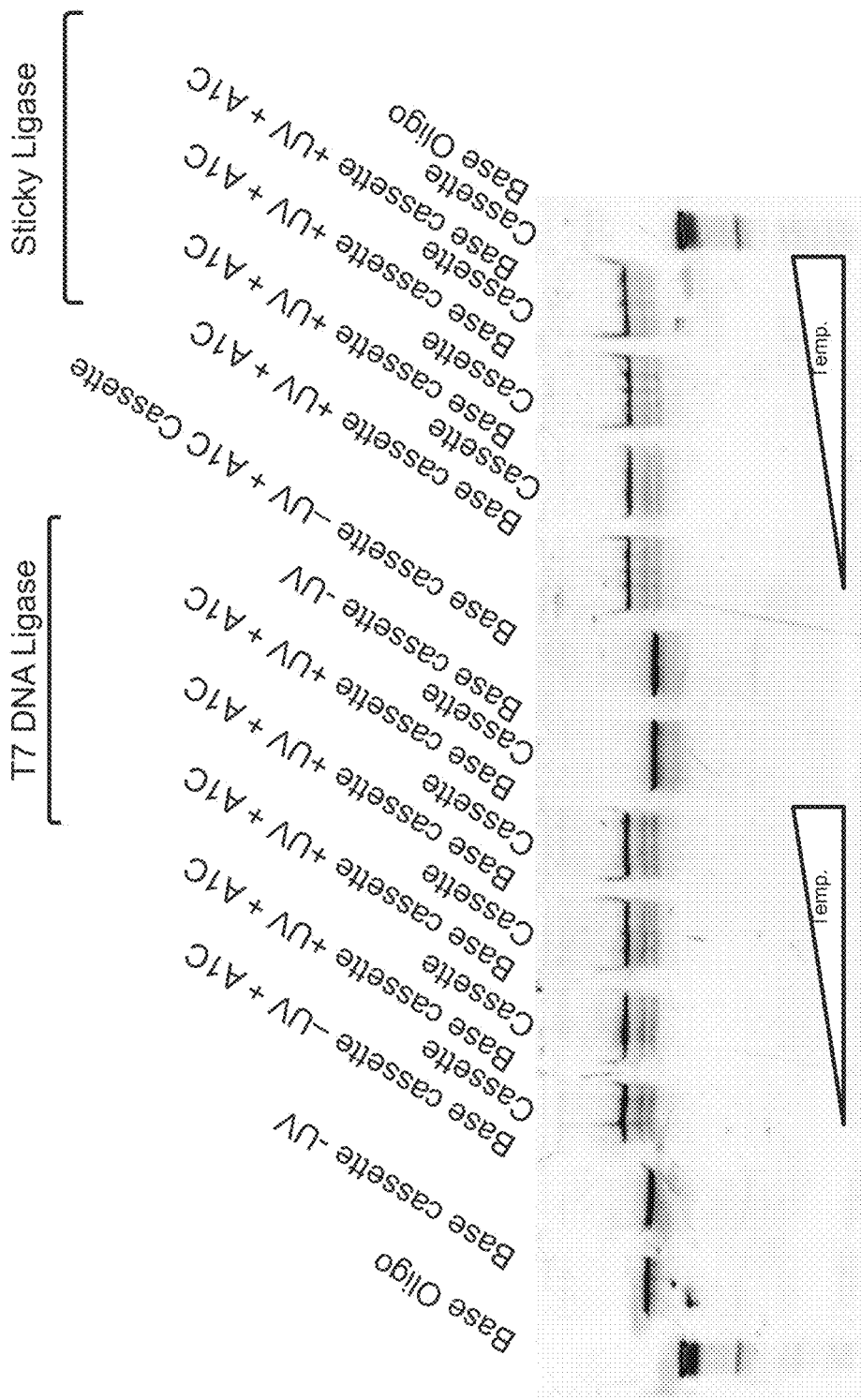
FIG. 8 shows an image of a group potential reaction sites with labels indicating which sites were exposed to UV to illustrate attachment between base cassette and DNA cassette in accordance with embodiments herein.

Referring to FIG. 8 a series of potential reaction sites are imaged. Only those sites wherein (+UV) is indicated, i.e., Base cassette+UV+A1C Cassette, does the A1C Cassette actually ligate to the base cassette since these are the only sites wherein the optical linker has been broken by the introduction of the +UV. For the sites labeled Base cassette-UV+A1C Cassette, the A1C Cassette did not attach to the Base cassette because the optical linker was not exposed to the UV and broken to reveal a sticky end to which the A1C Cassette could attach.

The major advantages of the embodiments here are twofold. First, the DNA is synthesized as large pools of oligomers, with each oligomer type representing a small portion of the binary data. This attribute is critical if DNA is to be used for data storage. In the exemplary embodiments described herein, the DLP is used to control the light at the pixel level and has the capability to direct light to millions of reaction sites simultaneously. This allows the synthesis of millions of specific DNA oligomers in a parallel process.

The second advantage to the embodiments described herein is the use of light based chemistry that allows deprotection to occur on the array surface, not in solution. By controlling the reaction at the immobilized surface, the array can be flooded with the DNA cassettes and the reactions are limited to the desired array location. In other processes the reaction needs to be isolated to individual wells, which requires dispensing the reagents to millions of sites; a process that is very difficult to scale-up.

One skilled in the art would appreciate variations and substitutes, including temperature ranges, timing ranges, light ranges and the like which would fall within the ordinary course of experimentation and thus are considered to be within the scope of the present embodiments. Additionally, one skilled in the art would appreciate the component substitutes which, though not listed out explicitly, would be known to one skilled in the art and thus considered to be within the scope of the present embodiments.

The invention claimed is:

1. A data storage system comprising:
a surface array including thereon multiple strands of immobilized double-stranded DNA oligomers, wherein a first end of each of the multiple strands is attached to the surface array and a second end of each of the multiple strands of immobilized double-stranded DNA oligomers is blunt such that both a forward and a reverse strand thereof are of equal lengths at the second end, and further wherein each of the multiple strands of immobilized double-stranded DNA oligomers includes a photocleavable optical linker at a first location of a forward strand of each of the multiple strands of immobilized double-stranded DNA oligomers;

an optical source for directing light at a first time to the surface array in a predetermined pattern, wherein when the light interacts with each photocleavable optical linker, a sticky end at the second end of each of the multiple strands of immobilized double-stranded DNA oligomers is exposed, while the first end of each of the multiple strands remains attached to the surface array;

multiple reagent wells storing data-encoded DNA cassettes, wherein each data-encoded DNA cassette includes a photocleavable optical linker at a first location of a forward strand of each of the data-encoded DNA cassettes;

means for introducing the data-encoded DNA cassettes to the surface array, wherein each of the data-encoded DNA cassettes is capable of being attached to an exposed sticky end, wherein, the optical source directs light to the surface array containing at least some combinations of the data-encoded DNA cassettes attached to the immobilized double-stranded DNA oligomers, wherein the light interacts with each photocleavable optical linker of each of the data-encoded DNA cassettes to create a sticky end at an unattached end of each of the data-encoded DNA cassettes; and further wherein additional data-encoded DNA cassettes from the multiple reagent wells are introduced to the surface array containing the combinations of the data-encoded DNA cassettes attached to the immobilized double-stranded DNA oligomers and at least some of the additional data-encoded DNA cassettes attach to the sticky end of at least some of the data-encoded DNA cassettes.

2. The data storage system of claim 1, wherein the optical source is a UV source.

3. The data storage system of claim 1, wherein the optical source is a digital light processor (DLP).

4. The data storage system of claim 1, further comprising:

means for making each attachment between a sticky end and a data-encoded DNA cassette permanent.

5. The data storage system of claim 1, wherein the surface array contains individually addressable pixels, each pixel including at least one strand of immobilized DNA and each pixel, including the at least one strand, being individually addressable by the optical source.

6. The data storage system of claim 5, wherein the surface array contains millions of pixels.

7. The data storage system of claim 6, wherein each pixel is 30 to 100 µm in size.

* * * * *

SEQUENCE LISTING

<160> NUMBER OF SEQ ID NOS: 25

<210> SEQ ID NO 1
<211> LENGTH: 65
<212> TYPE: DNA

```
<213> ORGANISM: Artificial Sequence
<220> FEATURE:
<223> OTHER INFORMATION: Synthetic

<400> SEQUENCE: 1
ctcacaaccc cagaaacaga catgcttcct gacatacgat atctgtgagc ttaatgtcct    60
tatgt                                                                65

<210> SEQ ID NO 2
<211> LENGTH: 11
<212> TYPE: DNA
<213> ORGANISM: Artificial Sequence
<220> FEATURE:
<223> OTHER INFORMATION: Synthetic

<400> SEQUENCE: 2
gttacacgga a                                                         11

<210> SEQ ID NO 3
<211> LENGTH: 11
<212> TYPE: DNA
<213> ORGANISM: Artificial Sequence
<220> FEATURE:
<223> OTHER INFORMATION: Synthetic

<400> SEQUENCE: 3
gttatacgga a                                                         11

<210> SEQ ID NO 4
<211> LENGTH: 11
<212> TYPE: DNA
<213> ORGANISM: Artificial Sequence
<220> FEATURE:
<223> OTHER INFORMATION: Synthetic

<400> SEQUENCE: 4
gttaatcgga a                                                         11

<210> SEQ ID NO 5
<211> LENGTH: 11
<212> TYPE: DNA
<213> ORGANISM: Artificial Sequence
<220> FEATURE:
<223> OTHER INFORMATION: Synthetic

<400> SEQUENCE: 5
gttagtcgga a                                                         11

<210> SEQ ID NO 6
<211> LENGTH: 11
<212> TYPE: DNA
<213> ORGANISM: Artificial Sequence
<220> FEATURE:
<223> OTHER INFORMATION: Synthetic

<400> SEQUENCE: 6
gttagctgga a                                                         11

<210> SEQ ID NO 7
<211> LENGTH: 11
<212> TYPE: DNA
<213> ORGANISM: Artificial Sequence
<220> FEATURE:
<223> OTHER INFORMATION: Synthetic

<400> SEQUENCE: 7
```
gttaactgga a                                                              11

<210> SEQ ID NO 8
<211> LENGTH: 11
<212> TYPE: DNA
<213> ORGANISM: Artificial Sequence
<220> FEATURE:
<223> OTHER INFORMATION: Synthetic

<400> SEQUENCE: 8
gttacgtgga a                                                              11

<210> SEQ ID NO 9
<211> LENGTH: 11
<212> TYPE: DNA
<213> ORGANISM: Artificial Sequence
<220> FEATURE:
<223> OTHER INFORMATION: Synthetic

<400> SEQUENCE: 9
gttatgtgga a                                                              11

<210> SEQ ID NO 10
<211> LENGTH: 11
<212> TYPE: DNA
<213> ORGANISM: Artificial Sequence
<220> FEATURE:
<223> OTHER INFORMATION: Synthetic

<400> SEQUENCE: 10
tacgcacgtt a                                                              11

<210> SEQ ID NO 11
<211> LENGTH: 11
<212> TYPE: DNA
<213> ORGANISM: Artificial Sequence
<220> FEATURE:
<223> OTHER INFORMATION: Synthetic

<400> SEQUENCE: 11
tacgtacgtt a                                                              11

<210> SEQ ID NO 12
<211> LENGTH: 11
<212> TYPE: DNA
<213> ORGANISM: Artificial Sequence
<220> FEATURE:
<223> OTHER INFORMATION: Synthetic

<400> SEQUENCE: 12
tacgatcgtt a                                                              11

<210> SEQ ID NO 13
<211> LENGTH: 11
<212> TYPE: DNA
<213> ORGANISM: Artificial Sequence
<220> FEATURE:
<223> OTHER INFORMATION: Synthetic

<400> SEQUENCE: 13
tacggtcgtt a                                                              11

<210> SEQ ID NO 14
<211> LENGTH: 11
<212> TYPE: DNA

<213> ORGANISM: Artificial Sequence
<220> FEATURE:
<223> OTHER INFORMATION: Synthetic

<400> SEQUENCE: 14
tacggctgtt a                                                                11

<210> SEQ ID NO 15
<211> LENGTH: 11
<212> TYPE: DNA
<213> ORGANISM: Artificial Sequence
<220> FEATURE:
<223> OTHER INFORMATION: Synthetic

<400> SEQUENCE: 15
tacgactgtt a                                                                11

<210> SEQ ID NO 16
<211> LENGTH: 11
<212> TYPE: DNA
<213> ORGANISM: Artificial Sequence
<220> FEATURE:
<223> OTHER INFORMATION: Synthetic

<400> SEQUENCE: 16
tacgcgtgtt a                                                                11

<210> SEQ ID NO 17
<211> LENGTH: 11
<212> TYPE: DNA
<213> ORGANISM: Artificial Sequence
<220> FEATURE:
<223> OTHER INFORMATION: Synthetic

<400> SEQUENCE: 17
tacgtgtgtt a                                                                11

<210> SEQ ID NO 18
<211> LENGTH: 11
<212> TYPE: DNA
<213> ORGANISM: Artificial Sequence
<220> FEATURE:
<223> OTHER INFORMATION: Synthetic

<400> SEQUENCE: 18
ggaacactac g                                                                11

<210> SEQ ID NO 19
<211> LENGTH: 11
<212> TYPE: DNA
<213> ORGANISM: Artificial Sequence
<220> FEATURE:
<223> OTHER INFORMATION: Synthetic

<400> SEQUENCE: 19
ggaatactac g                                                                11

<210> SEQ ID NO 20
<211> LENGTH: 11
<212> TYPE: DNA
<213> ORGANISM: Artificial Sequence
<220> FEATURE:
<223> OTHER INFORMATION: Synthetic

<400> SEQUENCE: 20
ggaaatctac g                                                                11

```
<210> SEQ ID NO 21
<211> LENGTH: 11
<212> TYPE: DNA
<213> ORGANISM: Artificial Sequence
<220> FEATURE:
<223> OTHER INFORMATION: Synthetic

<400> SEQUENCE: 21
ggaagtctac g                                                        11

<210> SEQ ID NO 22
<211> LENGTH: 11
<212> TYPE: DNA
<213> ORGANISM: Artificial Sequence
<220> FEATURE:
<223> OTHER INFORMATION: Synthetic

<400> SEQUENCE: 22
ggaagcttac g                                                        11

<210> SEQ ID NO 23
<211> LENGTH: 11
<212> TYPE: DNA
<213> ORGANISM: Artificial Sequence
<220> FEATURE:
<223> OTHER INFORMATION: Synthetic

<400> SEQUENCE: 23
ggaaacttac g                                                        11

<210> SEQ ID NO 24
<211> LENGTH: 11
<212> TYPE: DNA
<213> ORGANISM: Artificial Sequence
<220> FEATURE:
<223> OTHER INFORMATION: Synthetic

<400> SEQUENCE: 24
ggaacgttac g                                                        11

<210> SEQ ID NO 25
<211> LENGTH: 11
<212> TYPE: DNA
<213> ORGANISM: Artificial Sequence
<220> FEATURE:
<223> OTHER INFORMATION: Synthetic

<400> SEQUENCE: 25
ggaatgttac g                                                        11
```